United States Patent
Bauer et al.

(10) Patent No.: US 6,278,281 B1
(45) Date of Patent: *Aug. 21, 2001

(54) FLUID CONDITION MONITOR

(75) Inventors: Robert A. Bauer, South Milwaukee; Richard W. Hirthe, Milwaukee; Mark H. Polczynski, Elm Grove; Martin A. Seitz, Brookfield; James E. Hansen, Oak Creek, all of WI (US)

(73) Assignee: Eaton Corporation, Cleveland, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/220,556

(22) Filed: Dec. 23, 1998

(51) Int. Cl.$^7$ ............................. G01N 27/02; G01R 27/26

(52) U.S. Cl. ........................................... 324/441; 324/668

(58) Field of Search ..................................... 324/441, 439, 324/442, 444, 668, 670

(56) References Cited

U.S. PATENT DOCUMENTS

| | | | |
|---|---|---|---|
| 4,560,923 | * 12/1985 | Hanson | 324/668 |
| 4,646,070 | 2/1987 | Yasuhara et al. | 340/603 |
| 4,692,685 | 9/1987 | Blaze | 324/61 QS |
| 4,733,556 | 3/1988 | Meitzler et al. | 73/64 |
| 4,743,855 | 5/1988 | Randin et al. | 324/430 |
| 5,274,335 | 12/1993 | Wang et al. | 324/689 |
| 5,418,466 | * 5/1995 | Watson et al. | 324/668 |
| 5,526,808 | 6/1996 | Kaminsky | 128/632 |
| 5,644,239 | * 7/1997 | Huang et al. | 324/441 |
| 5,708,363 | * 1/1998 | Yates et al. | 324/442 |
| 5,824,889 | 10/1998 | Park et al. | 73/116 |

FOREIGN PATENT DOCUMENTS

| | | |
|---|---|---|
| 1498815 | 4/1969 | (DE). |
| 195 40 507 | 5/1997 | (DE). |
| 57108650 | 7/1982 | (JP). |
| WO 9850790 | 11/1998 | (WO). |

OTHER PUBLICATIONS

W. Fichtner, H. Kaden & W. Schindler: "On–line–Messugn der Eigenschaften von Schmierolen fur Verbrennungsmotoren mit einem elektrischen Sensor". Technisches Messen 65 (1998) 2.

(List continued on next page.)

*Primary Examiner*—Safet Metjahic
*Assistant Examiner*—J Kerveros
(74) *Attorney, Agent, or Firm*—Roger A. Johnsto n

(57) ABSTRACT

A fluid condition monitor suitable for real time monitoring of a fluid in a fluid system such as on-board vehicle monitoring of engine oil and transmission fluid to determine contamination. A capacitive spaced array electrode probe is immersed in the fluid and an oscillating voltage is applied at a first frequency of at least one hertz and the current $I_B$ measured as an analog of the bulk fluid impedance. The voltage is also applied to the probe at a second frequency of less then one hertz and the current $I_s$ measured as an analog of the electrode surface impedance. The difference in measured currents $\Delta I$ is determined electrically compared with a predetermined threshold value; and, the measured first frequency current $I_B$ is compared with an upper and lower limit value for $I_B$ determined empirically for the known baseline fluid. If $\Delta I$ is below the threshold or $I_B$ is not within the upper and lower limits, a fault condition is declared and an indicator is activated to warn that the fluid is not suitable for continued operation of the system. An alternate embodiment includes a fluid level sensor.

19 Claims, 13 Drawing Sheets

OTHER PUBLICATIONS

"The Applications of AC Impedance Technique For Detecting Glycol Contamination in Engine Oil" by S. S. Wang, et al., published Jan. 4, 1997 by Elsevier Science S.A.

"Novel Sensors for Portable Oil Analyzers" Case Western Reserve University, Cleveland, Ohio Dept. of Physics NTIS 19980624 080.

"AC Impedance Measurements of the Resistance and Capacitance of Lubricants" by S. S. Wang, et al, published Jun. 13, 1986 ASLE Transactions vol. 30, 4, 436–443.

The Development of in situ Electrochemical Oil–Condition Sensors by S. S. Wang, et al., Published 1974 by Elsevier Sequoia.

"On–board Monitoring of Properties of Lubricating Oils for Combustion Engines Using an Electric Sensor" by Fichtner, Wolfgang; Kaden, Heiner; Schindler, Wolfgang *Technisches Messen 65* (1998) 2:53–57 ©R. Oldenburg Verlag (Publisher) Missing Month.

* cited by examiner

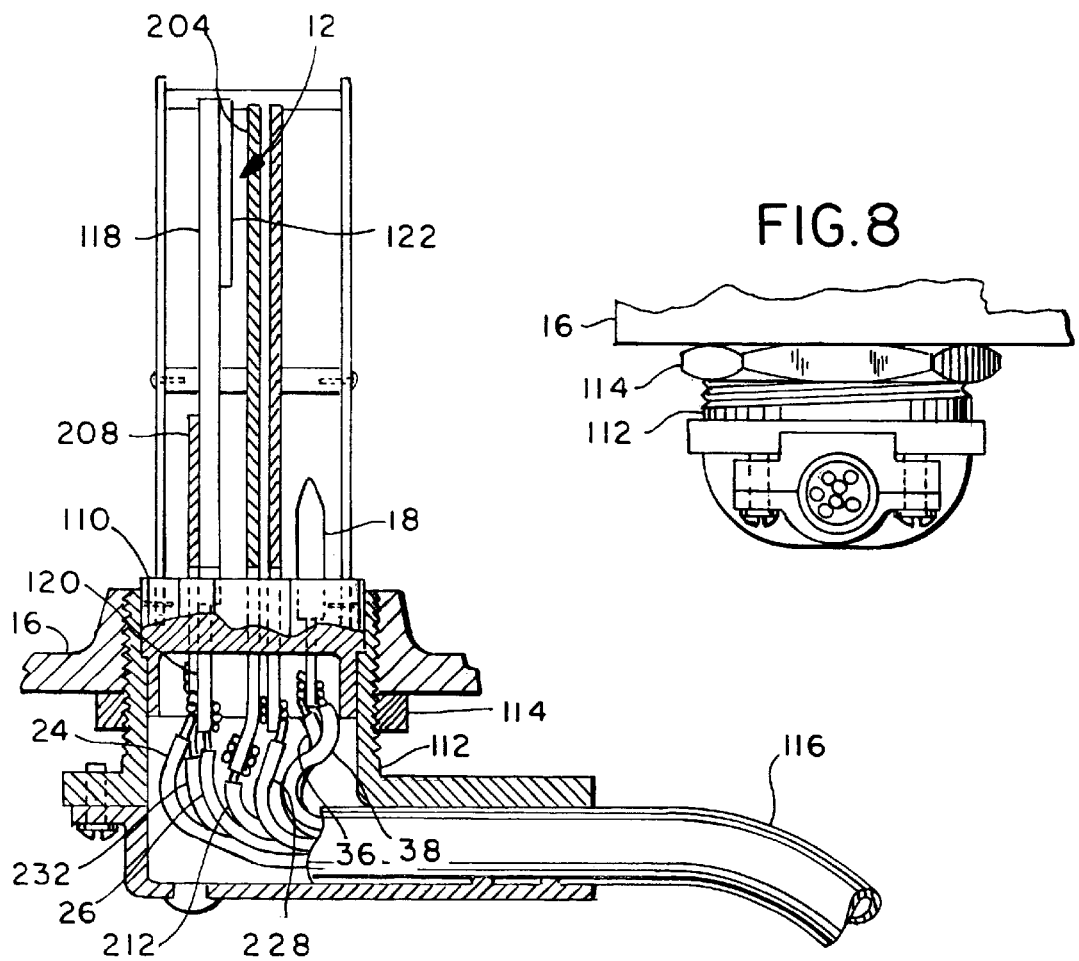
FIG.8
FIG.6
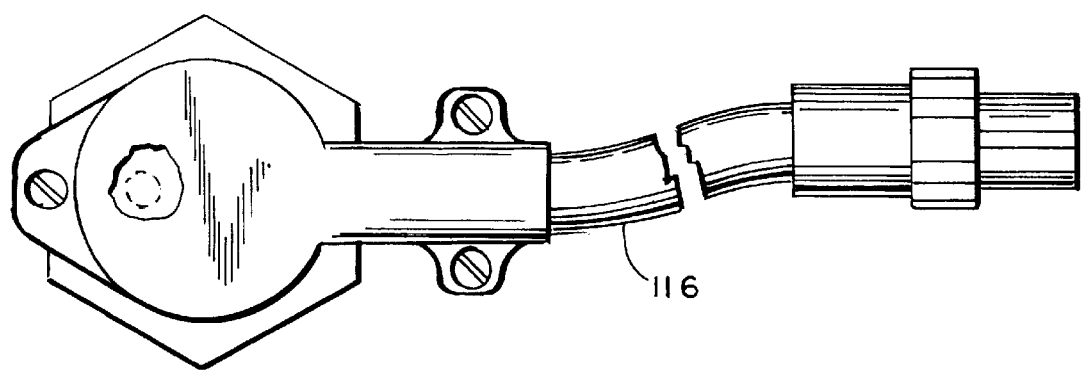
FIG.7

FLUID CONDITION MONITOR

CROSS-REFERENCE TO RELATED APPLICATIONS

Not Applicable

STATEMENT REGARDING FEDERALLY SPONSORED RESEARCH OR DEVELOPMENT

Not Applicable

MICROFICHE APPENDIX

Not Applicable

BACKGROUND OF THE INVENTION

The present invention relates to devices or systems for monitoring the condition of a working fluid in a system, as for example, lubricating oil in an engine or power transmission device where the oil is subject to contamination by introduction of foreign substances such as engine coolant or deterioration due to chemical activity from products of combustion or aging.

In the operation of motor vehicles, it has long been desired to have the capability to monitor the fluid in the power transmission components such as the engine and power transmissions on a real time or running basis during operation of the vehicle and to have the capability to provide a warning or indication to the vehicle operator that the lubricating fluid has reached a state of contamination or deterioration so as to be considered unsuitable for continued operation. Heretofore, attempts have been made to utilize alternating current impedance spectroscopy to detect the change in impedance of a low level current flowing through a capacitor immersed in the fluid. Examples of such known systems employing AC electro-impedance spectroscopy are those described in U.S. Pat. No. 4,733,556 issued to Meitzler, et al., U.S. Pat. No. 5,274,335 issued to Wang, et al., and U.S. Pat. No. 4,646,070 issued to Yasuhara, et al. These systems describe the application of electro-impedance spectroscopy techniques for determining the condition of internal combustion engine lubricating oil due to contamination with engine coolant and to deterioration due to the chemical effect of the products of combustion and aging on the engine lubricating oil. The aforesaid known systems employ the technique of applying an AC signal current relatively high frequency to the plates of a capacitor and determining the change in the impedance measured thereon. Typically such frequencies are in the multi-hertzian range of generally between 10 hertz and 500 kilohertz.

One known report of earlier work is that described in the publication "The Applications Of AC Impedance Technique For Detecting Glycol Contamination In Engine Oil" by S. S. Wang, et al. published Jan. 4, 1997 by Elsevier Science S.A. This later work describes scanning the immersed capacitor with a sinusoidal voltage of 2.5 volts peak over a range of frequencies from one milli-hertz to one kilohertz. However this later work utilized only the bulk resistance of the fluid as determined by utilizing frequencies in the range between 100 hertz and 1 kilohertz and is not suitable for on-board continuous fluid monitoring.

However, none of the aforesaid prior art systems have provided a low cost and useable technique for on-board vehicle monitoring of the condition of the lubricating fluids and, thus it has been desired to provide a way or means of providing a simple low cost system for indicating contamination or deterioration of lubricating fluids, particularly those in motor vehicle engine and power transmission applications.

BRIEF SUMMARY OF THE INVENTION

The present invention provides a useful and novel technique of employing AC electro-impedance spectroscopy to monitor the condition of working fluids such as lubricant, and which is suitable for on-board motor vehicle use to enable real time monitoring of the condition of the lubricating oil in the engine or transmission.

The present invention employs a low level oscillating voltage signal across the plates or spaced electrodes of a capacitor immersed in the fluid to be monitored and measures the current of the signal applied at a first or high frequency associated with the bulk impedance of the fluid and at a second low frequency associated with the electrochemical properties of the surface of the electrode and determines the difference of the first and second measured currents. The current measured for the higher frequency is compared with measurements at the same frequency for acceptable fluid to determine if the current reading for the higher frequency associated with bulk impedance measurements is within predetermined limits. The difference in currents is compared with a predetermined threshold and if both aforesaid conditions are met, the fluid is considered to be suitable for continued operation; however, if either condition is not met, the monitor provides an electrical indication that the fluid is not suitable for continued operation.

In the preferred embodiment, current is measured and converted to a voltage for purposes of the comparison.

In a second embodiment the electrodes of the capacitance are positioned adjacent separate plate-type electrodes which have the first high frequency signal voltage applied also thereto for fluid level detection purposes; and, the circuitry for monitoring the fluid condition detecting capacitance is disabled if the level detector indicates a low-level condition.

The present invention thus provides a simple, low cost technique for real time onboard monitoring of lubricating fluid employed in engines and power transmissions of motor vehicles and other working fluid system applications.

BRIEF DESCRIPTION OF THE DRAWINGS

FIG. 6 is a section view of the fluid condition monitoring probe of the system of FIG. 1;

FIG. 7 is a bottom view of the probe of FIG. 6;

FIG. 8 is a right-hand end view of the probe assembly of FIG. 6;

DETAILED DESCRIPTION OF THE INVENTION

Figure 1:
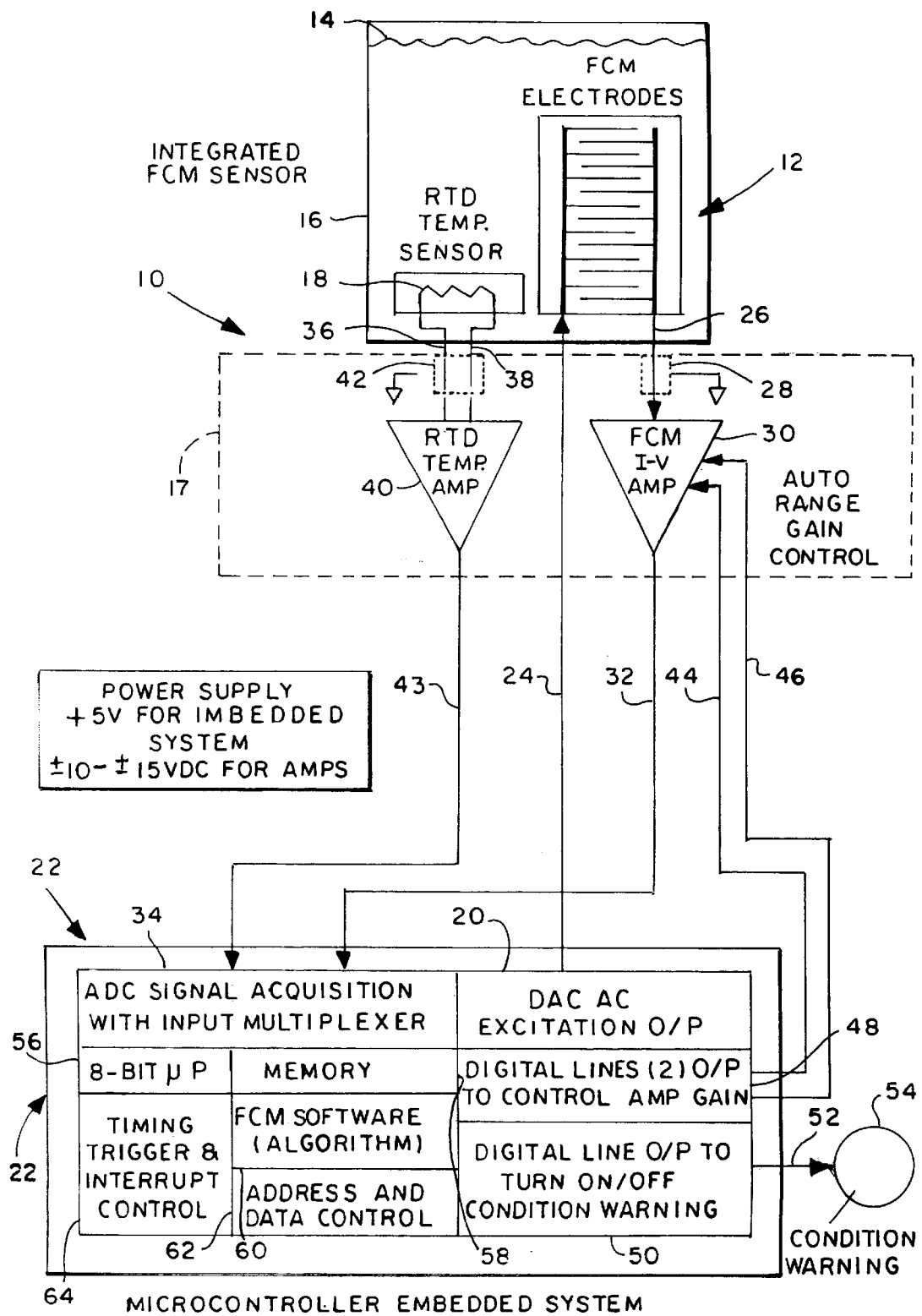
FIG. 1 is a block diagram of the present invention in its simplest form.

Referring to FIG. 1, the basic system of the invention is indicated generally at 10 as having a probe assembly indicated generally at 12 which is immersed at least partially in fluid 14 contained in a receptacle 16 which may be an engine crankcase or power transmission housing or other fluid vessel. The probe assembly will be described in greater detail hereinafter; and, a temperature sensor comprising a resistive temperature device 18 is also immersed in the fluid 14. The probe 12 receives an input along line 24 from the AC excitation section 20 of the microprocessor base microcontroller, indicated generally at 22, and, the output of the probe assembly 12 is provided along line 26, which has a grounded shield 28, to the input of an amplifier and current to voltage converter 30 which has its output connected along line 32 to the signal acquisition section 34 of microcontroller 22. The temperature sensor 18 is connected through lines 36, 38 with the lines having a grounded shield 42 to the input of an amplifier 40. The output of the amplifier 40 is also connected along line 43 to the signal acquisition section 34. The amplifier/current to voltage converter 30 has an "auto range" gain control function and is connected to receive inputs along lines 44, 46 from digital controller section 48 of microcontroller 22. The microcontroller has a digital output line section 50 which is connected along line 52 to a condition warning indicator 54 to provide excitation thereof.

The microcontroller 22 includes an eight bit microprocessor 56, a memory section 58, embedded software containing the algorithm for probe 12, as denoted by section 60, and an address and data control function section 62 with the timing trigger and interrupt control being performed by section 64.

It will be understood that the probe 12 and temp sensor 18 may be mounted on a common support structure for connection through an opening in the housing or casing 16.

The temp sensor 40 is conventionally connected in a Wheatstone bridge circuit and forms one leg thereof; and, therefore the details of the circuit therefor have been omitted for the sake of brevity. In the present practice of the invention, the sensor 18 is a platinum element on a ceramic substrate and has a resistance change proportional to temperature with a nominal resistance of 100 ohms at 0° Centigrade and a positive temperature coefficient of 0.00385 ohms per ohm per degree Centigrade. A suitable ceramic substrate employed in the present practice of the invention measured about 2 by 2 by 1.3 millimeters. In the present practice of the invention the sensor 18 was surrounded by a protective copper tube (not shown in FIG. 1).

In the presently preferred practice of the invention the amplifiers 30, 40 are mounted as close to the housing or casing 16 as is practical and may be enclosed in a suitable protective enclosure denoted by reference numeral 17 and illustrated in dashed outline in FIG. 1. Such an arrangement keeps the length of the shielded cables 42, 28 to a minimum and reduces signal loss between the probe 12 and temperature sensor 18 and their respective amplifiers.

Figure 3:
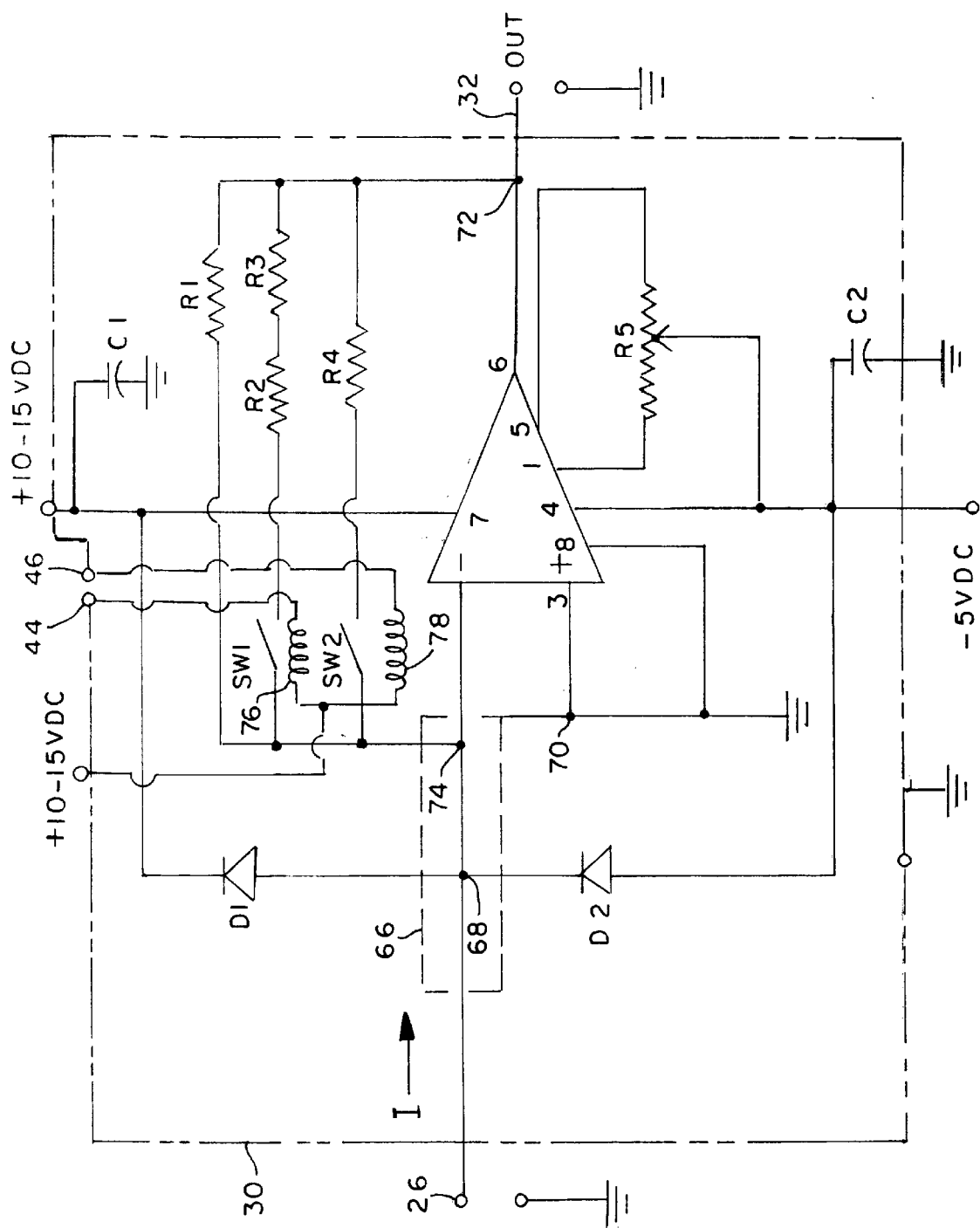
FIG. 3 is a circuit schematic for the amplifier and current voltage converter for the system of FIG. 1.

Referring to FIG. 3, amplifier 30 receives a current signal from probe output line 26 at its input connection which signal is applied to the inverting input of device IC-1 which is protected by a guard ring shown in dashed outline denoted by reference numeral 66. The probe 12 is excited by a constant supply voltage having a 1.0 volts A.C. RMS, 1.6 volts peak magnitude at a first and second oscillation frequency preferably comprising a sinusoidal alternating zero crossing wave form. It will be understood however that other forms of oscillating voltage may be employed.

Diodes D1 and D2 prevent the input from being driven above or below the power supply voltage and are connected to the input line at junction 68 and respectively to pins 7 and 4 of IC-1. In the present practice of the invention the device IC-1 is a Burr-Brown Part No. OPA128 or may comprise an analog device part No. 549 current to voltage conversion device. The positive input of IC-1 is grounded through junction 70. The output of IC-1 is connected to line 32 through junction 72 which also is connected through a resistor network to junction 74 which is connected to the input line of IC-1. The resistor network includes R1 connected on a leg between junction 72 and junction 74 and a leg connected in parallel therewith comprising switch SW1 and series resistors R2 and R3. Another leg is also connected in parallel with R1 and comprises switch SW2 in series with resistor R4. The resistor network is required to automatically adjust the gain due to the three decade swing of the input current signal from the probe 12. The computer sequentially activates the switches SW1, SW2 to close to maintain output voltage at plus or minus 8.5 volts peak 6 volts A.C. RMS. Resistor R5 connected between pins 5 and 1 of IC-1 is a variable potentiometer provided for zero adjustment.

In the presently preferred practice, the switches SW1, SW2 are magnetically actuated glass reed switches and are closed by energization of the relay coils denoted respectively 76, 78 which are connected each along one of the lines 44, 46 on one side thereof; and, the opposite side of each coil 76, 78 is connected to receive 10 to 15 volts DC from the power supply. The resistor network serves to adjust the gain of the device IC-1 by changing the level of resistance in the feedback loop comprising the resistor network.

The default gain with SW1 and SW2 both open is only R1 acting as the feedback resistor and provides a conversion of one volt per nano-amp input to IC-1. With SW1 closed, the effective resistance of resistors R1, R2 and R3 provides a conversion of 0.1 volts per nano-amp; and, with SW1 and SW2 both closed and R4 connected to the network, the effective gain is 1.01 volt per nano-amp. SW1 and SW2 being glass reed relays provide extremely high leakage resistance and low capacitance. When probe signal acquisition is started, the acquisition section 34 determines if any of the amplifier outputs is being driven to near-saturation. If this is the case, the acquisition is restarted with a gain of that amplifier indexed to the next lower condition and restarted. If saturation again occurs at any current flow, its gain is further indexed to the lowest level. Thus, the gain of the amplifier 30 is adjusted individually as needed until a complete acquisition sequence can be accomplished. The acquisition section 34 accomplishes this by "auto ranging" by responding to saturation by sending a logic signal to the control amp gain section 48 which in turn supplies current signals to the respective relay coils in the amplifier section 30 for controlling switches SW1, SW2. It has been determined that the probe 12 needs to function at temperatures up to 90° Centigrade and thus a range of multiple decades of amplifier gain control may be required.

Referring to FIG. 3, the designation and values for the various electronic components of the circuit are set forth in Table I below.

TABLE I

| Device Designation | Type/Value |
| --- | --- |
| IC-1 | CPA128, AD549 |
| D1, D2 | 2N4117 |
| R1 | 1G Ohm |
| R2 | 100 Meg Ohm |
| R3, R4 | 11 Meg Ohm |
| R5 | 50K Ohm, Variable |
| C1, C2 | 0.1 u fd |
| SW1, SW2 Coil | 700 Ohm, 5 V |
| SW1, SW2 | EAC R1A5AHH |

Figure 4:
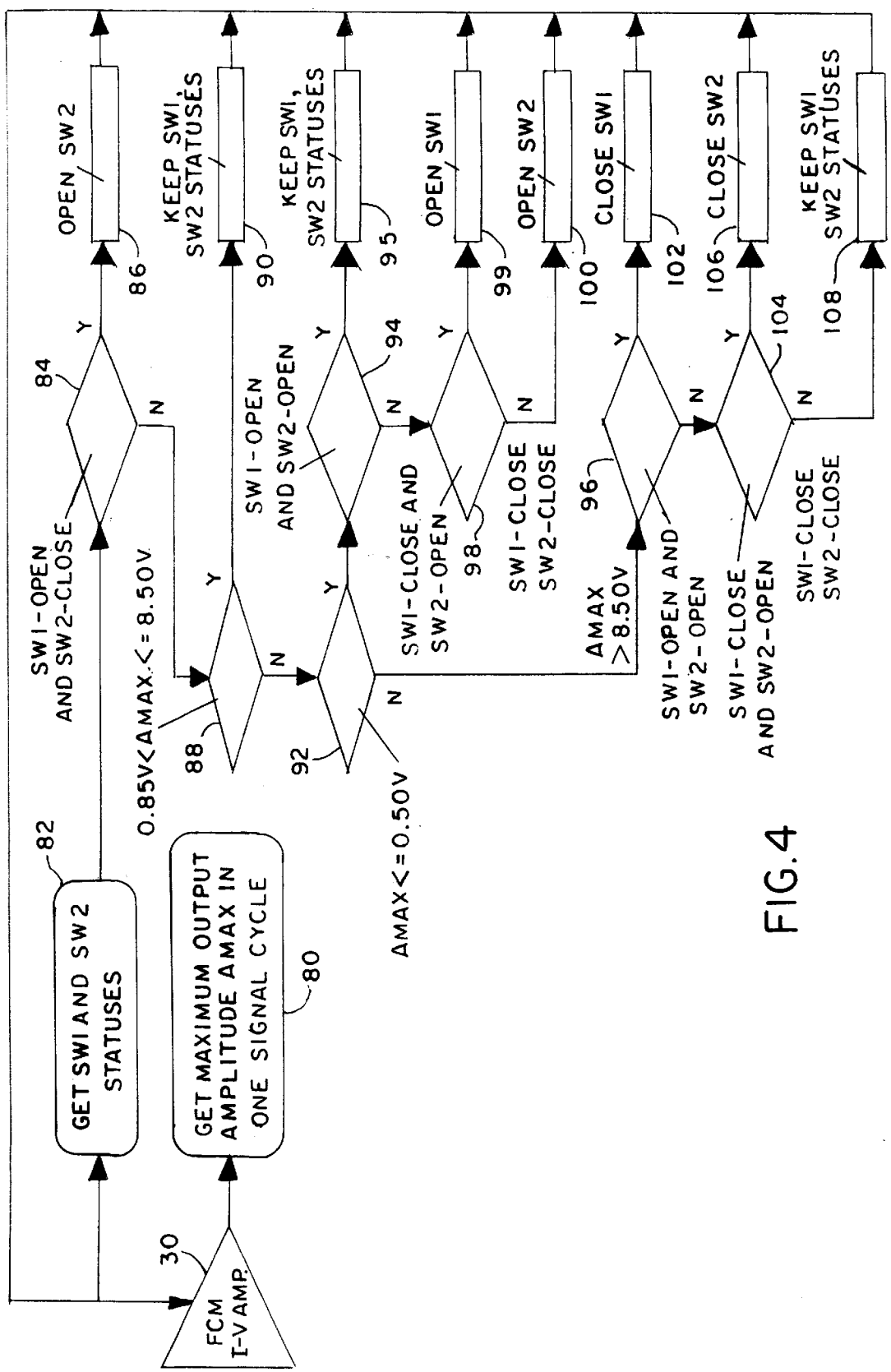
FIG. 4 is a block diagram of the control logic for the switches of FIG. 3.

Referring to FIG. 4, the system control functions are illustrated in the form of a block diagram in which the maximum output of amplifier 30 is determined for a given signal cycle at step 80 and the status of switches SW1, SW2 is determined at step 82. The status from step 82 is utilized at step 84 to determine whether SW1 is open and switch SW2 is closed. If the determination is affirmative, the system proceeds to step 86 to open switch SW2 and change the gain of IC-1 to the next higher level. If however, the determination at step 84 is negative, the system proceeds to step 88 to determine if the amplitude $A_{max}$ is greater than 0.85 volts and equal to or less than 8.50 volts. If the determination at step 88 is positive, the system proceeds to step 90 to maintain the existing status of switches SW1, SW2.

If the determination at step 88 is negative, the system proceeds to step 92 to determine if $A_{max}$ is equal to or less than 0.85 volts; and, if affirmative, the system proceeds to step 94 and asks if SW1 and SW2 are both open. If the determination at step 92 is negative and a $A_{max}$ is greater than 8.50 volts, the system proceeds to step 96 and asks if SW1 and SW2 are both open.

If the determination at step 94 is negative, the system proceeds to step 98 and asks if SW1 is closed and SW2 is open. If the determination at step 94 is positive the system proceeds to step 95 and maintains the status of SW1 and SW2.

If the determination at step 98 is positive, the system opens switch SW1 at step 99. If the determination at step 98 is negative implying that SW1 and SW2 are both closed, the system proceeds to open switch SW2 at step 100.

If the system determines at step 96 that SW1 and SW2 are open, the system proceeds to step 102 and closes switch SW1.

If the determination at step 96 is negative, the system proceeds to step 104 and asks whether SW1 is closed and SW2 is open. If the response to step 104 is affirmative, the system proceeds to step 106 to close switch SW2. If the determination at step 104 is negative implying SW1 and SW2 are both closed, the system proceeds to step 108 to keep the status of SW1 and SW2.

The truth table for the flow diagram of FIG. 4 is set forth in Table II below.

TABLE II

| Switch Position | Resistance | Gain |
| --- | --- | --- |
| SW1 OPEN<br>SW2 OPEN | R1 | 1 Volt/nano amp. |
| SW1 CLOSED<br>SW2 OPEN | $\frac{R1\,(R_2 + R_3)}{R1 + R_2 + R_3} = 100$ Meg | 0.1 Volt/nano amp. |
| SW1 CLOSED<br>SW2 CLOSED | $\frac{R_4 \times 100 \text{ Meg}}{R_4 + 100 \text{ Meg}}$ | 0.01 Volt/nano amp. |

Referring to FIGS. 6, 7 and 8, the mechanical construction of the probe 12 is shown as mounted on a base 110 which is mounted to a tubular hollow receptacle 112 which is threadedly engaged in an aperture provided through the wall of the casing or wall of fluid vessel 16 and secured therein by a lock nut 114. In the present practice of the invention the receptacle 112 has a right angle configuration for receiving therein a cable 116 which contains the leads for electrical connection to the probe 12 and the temperature sensor 18. If desired, base 110 may have additional devices attached thereto as will be described hereinafter with respect to the embodiment of FIGS. 10 and 11. The probe 12 is supported by a supporting plate 118 which extends from the base 110 upwardly into the surrounding fluid within the casing, 16. Electrical terminals such as terminal 120 extend from the support structure 118 through the base 110 to provide for electrical connection the leads 24, 26.

Figure 9:
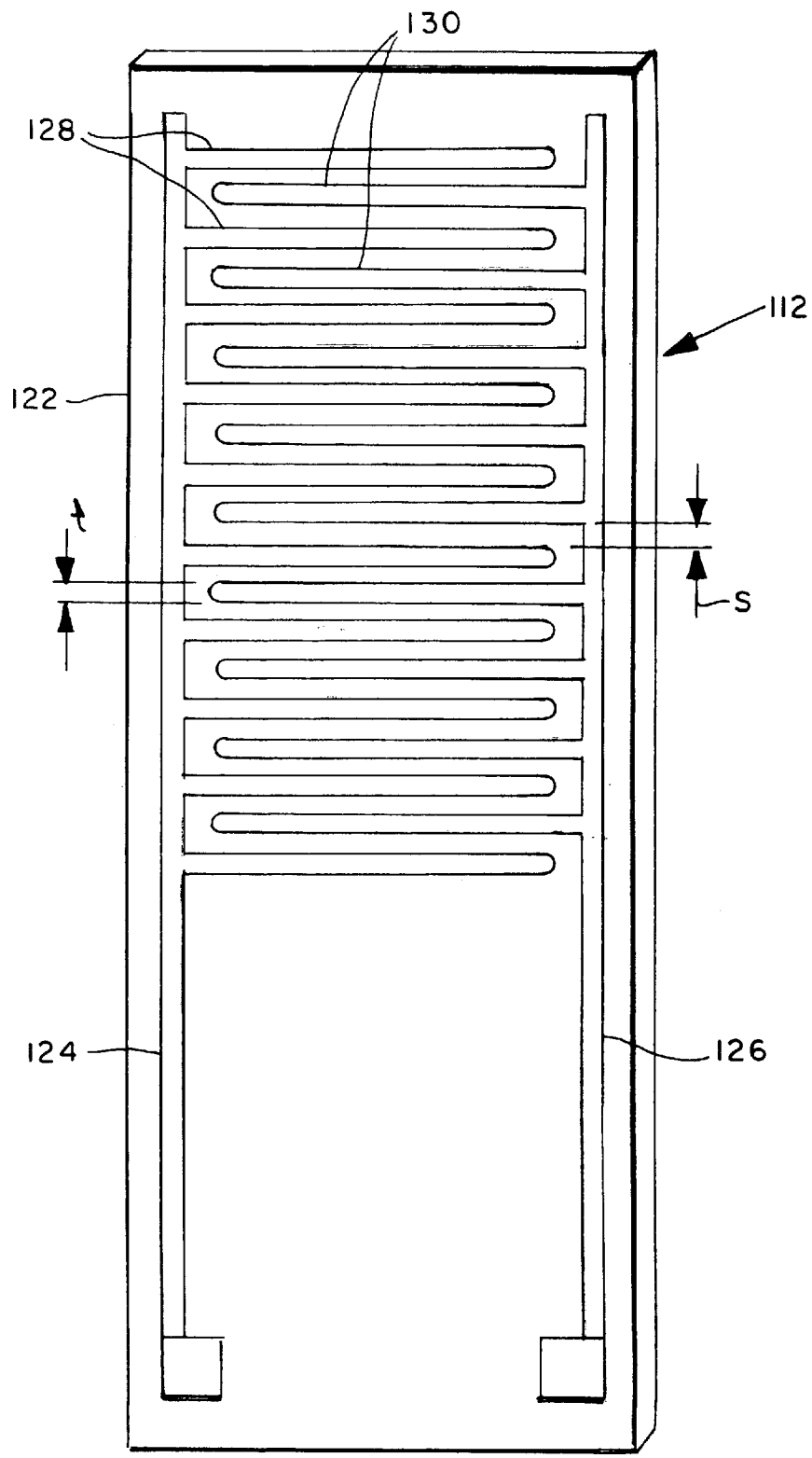
FIG. 9 is a detailed view of the configuration of the electrodes for the fluid monitoring probe of FIG. 1.

Referring to FIG. 9, the probe 12 is shown in the preferred practice as mounted on a substrate 122 which comprises a glass filled polytetrafluoroethylene (PTFE) substrate; and, the substrate 122 is mounted on the support structure 118 which preferably is formed of a high dielectric material such as polyetherimide plastic.

In the presently preferred practice of the invention the probe 12 includes two spaced electrodes 124, 126 formed on the substrate 122 with interdigitated fingers extending therefrom as illustrated in FIG. 9 to form an array of interdigitated parallel capacitive elements for each electrode denoted respectively by reference numerals 128, 130. In the present practice of the invention, the array of electrodes 124, 126 has a length of about two inches and a width of about one inch with the thickness denoted by dimension t in FIG. 9 of about 0.040 inches (1.0 millimeters). In the presently preferred practice of the invention, the spacing, denoted by reference character S in FIG. 9, is chosen in the range of about 0.127 millimeters to about 1.0 millimeters.

The electrodes 124, 126 can be formed by milling material from a printed circuit board comprising glass filed PTFE with a metal surface coated thereon of about 0.108 millimeters with an electroplated Nickel coating thereover of about 0.005 millimeters. Alternatively, the electrodes may be deposited on a glass filled PTFE substrate by photolithography comprising a Titanium coating of about Angstrom thickness coated with a Nickel sputtered coating of about 1 micron thickness and plated with a Nickel coating of about 200 to about 400 micro inches (508 to $1016 \times 10^8$ Angstroms).

In the present practice of the invention, the substrate 122 of the probe 12 is formed of a material having a low dielectric constant (high dielectric properties), a high bulk resistance and a high surface resistance preferably not less than $10^{12}$ Ohm-cm.

Figure 5:
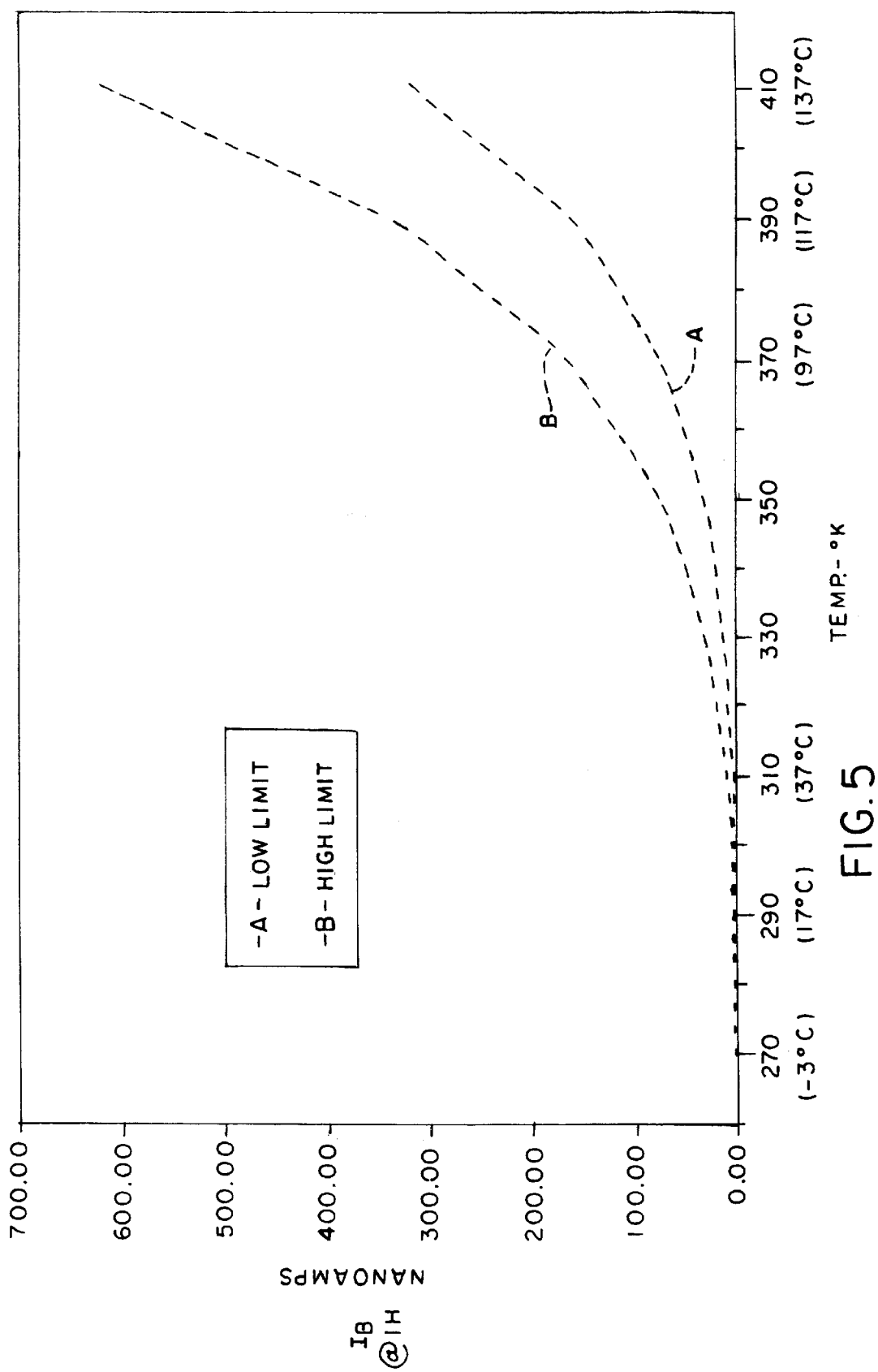
FIG. 5 is a plot of current measured at the higher frequency for the system of FIG. 1 plotted as a function of temperature.

Referring to FIG. 5, data has been plotted for measurements of the current flow through the electrodes of probe 12 for numerous samples of lubricating fluid such as lubricant for heavy duty truck transmissions (HDTT), automatic transmission fluid and passenger car motor oil (PCMO) at the higher frequencies of at least one hertz to determine the current IB due to changes in the bulk impedance of the fluid over a broad range of temperatures from 270° to 410° Kelvin. The band spread of the data were evaluated to provide an upper or high limit curve denoted by reference character B in FIG. 5 and a curve for the lower limit of values denoted by reference character A in FIG. 5. The various fluids of interest which were evaluated have the current values $I_B$, corresponding to the variation in bulk impedance as measured at 1 hertz, falling within a regime bounded by the curves for the high and low limit in FIG. 5. In the present practice of the invention, the data for the curves were entered into a Microsoft Excel Spreadsheet "LINEST" Multiple Regression Function and the expressions for the curves determined to be as follow.

$$\text{High limit} = 1.15(10^{8.1516 - 2222.4/(T+273.15)})$$

$$\text{Low limit} = 0.85 \times 10^{(8.5489 - 2451.53/(T+273.15))}$$

Figure 12:
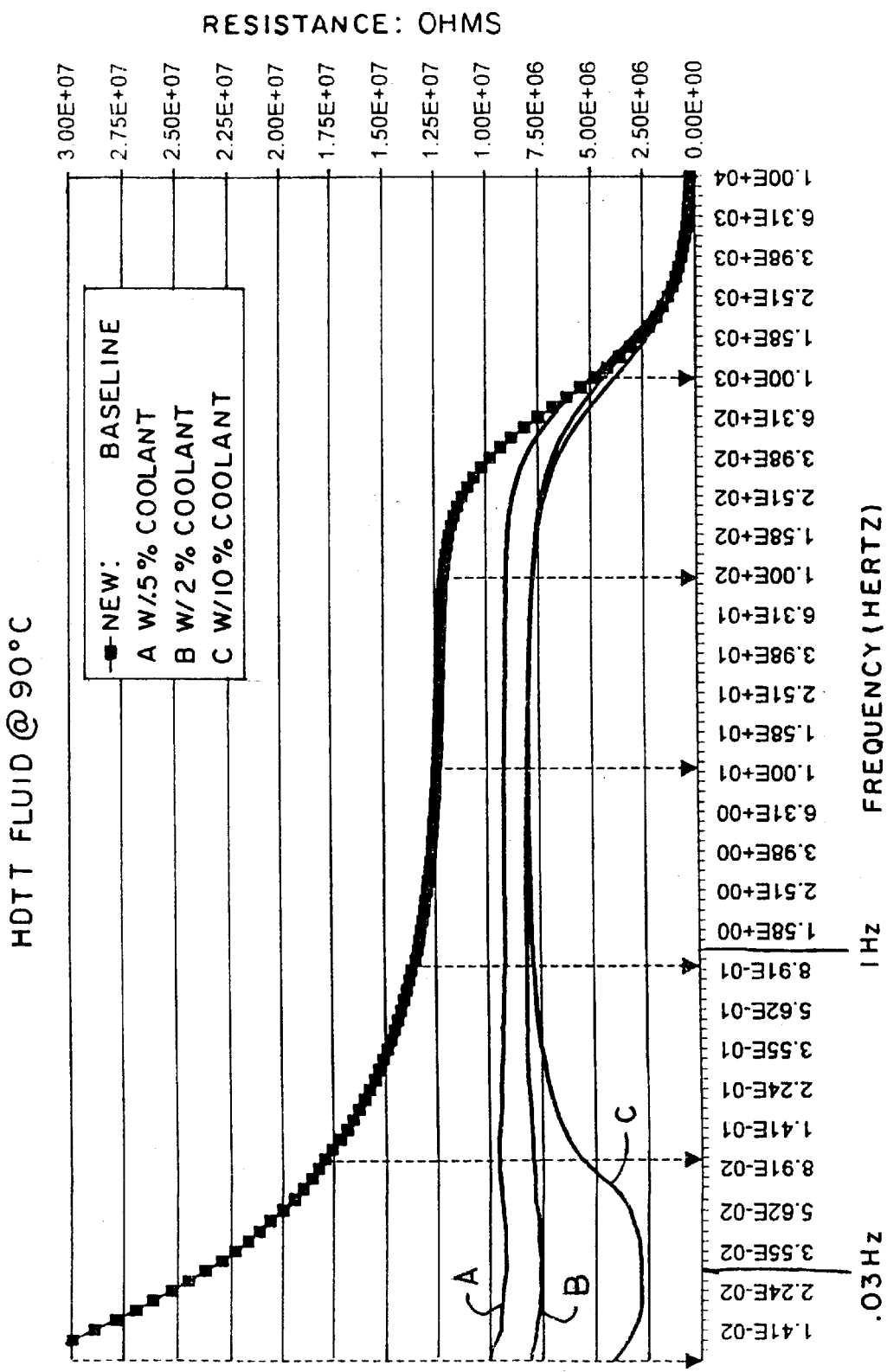
FIG. 12 is a Bode plot of frequency versus resistance for three levels of engine coolant contamination for new heavy duty truck transmission synthetic lubricant.
Figure 13:
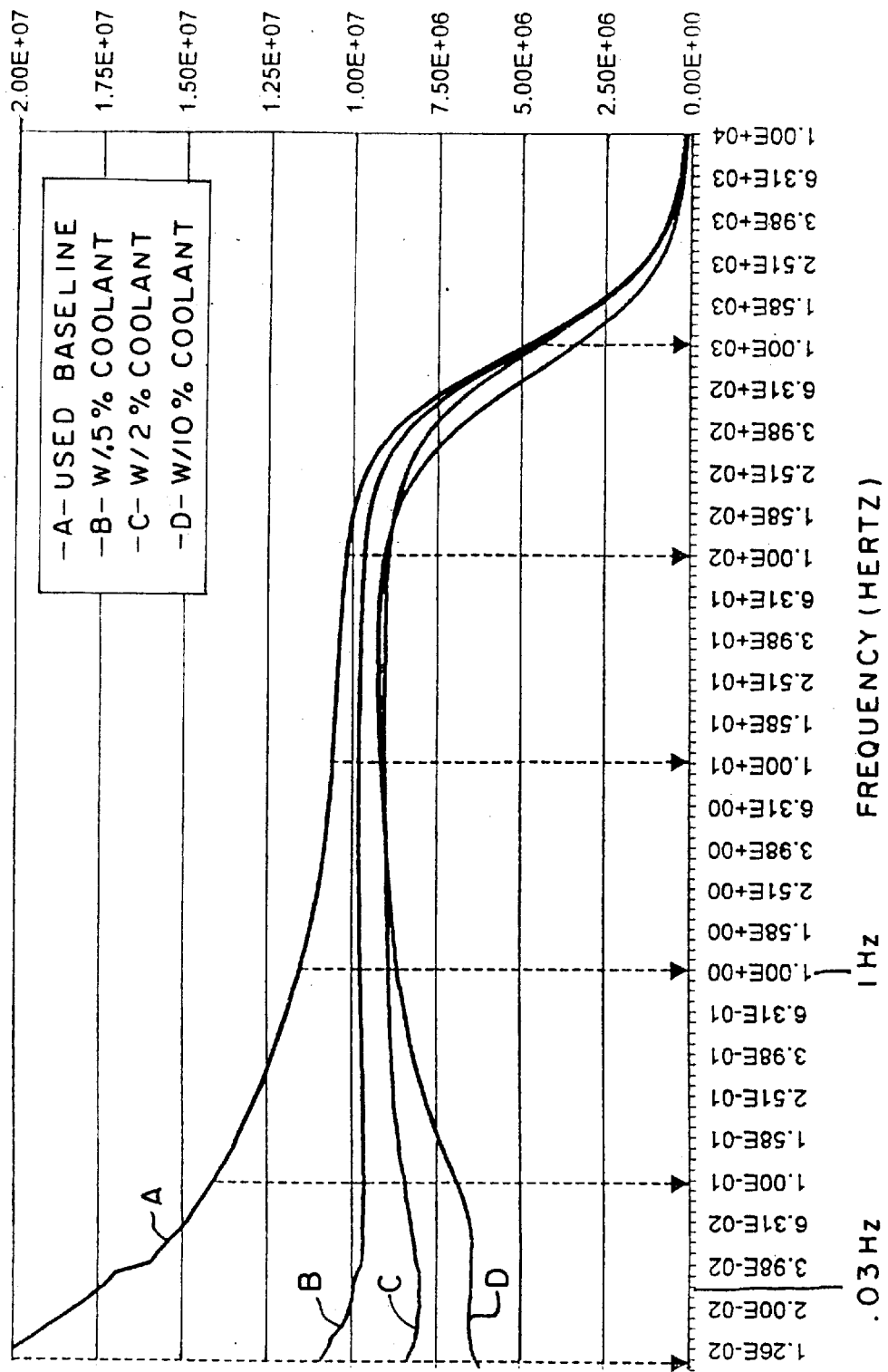
FIG. 13 is a Bode plot similar to FIG. 12 for three levels of coolant contamination of used synthetic heavy duty truck transmission fluid.
Figure 14:
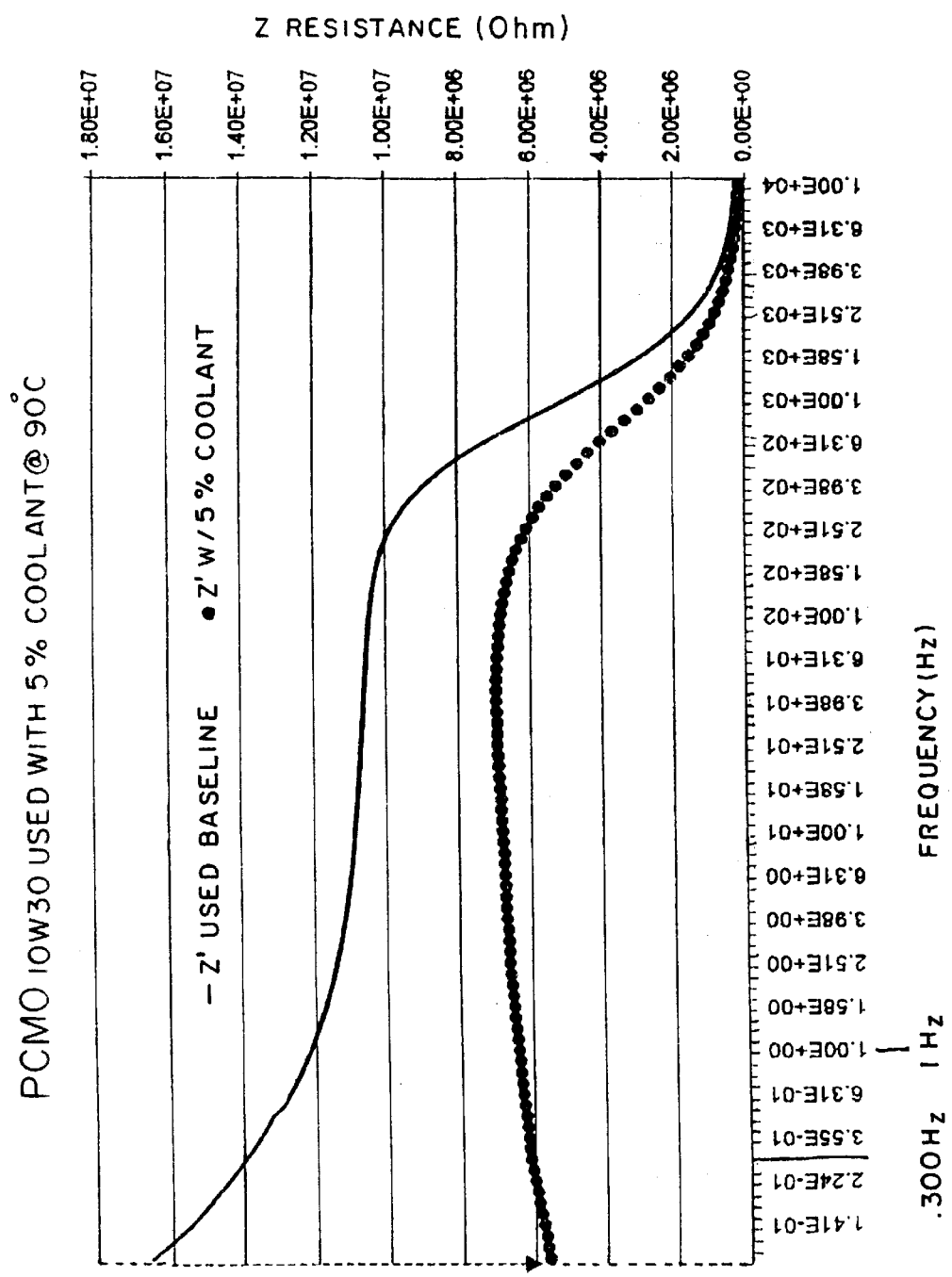
FIG. 14 is a Bode plot of resistance versus frequency for measurements taken of synthetic 10W30 used passenger car engine drain oil with 5% engine coolant contaminant; and, FIG. 15 is a Bode plot of frequency versus resistance for measurements taken of automatic transmission fluid.
Figure 15:
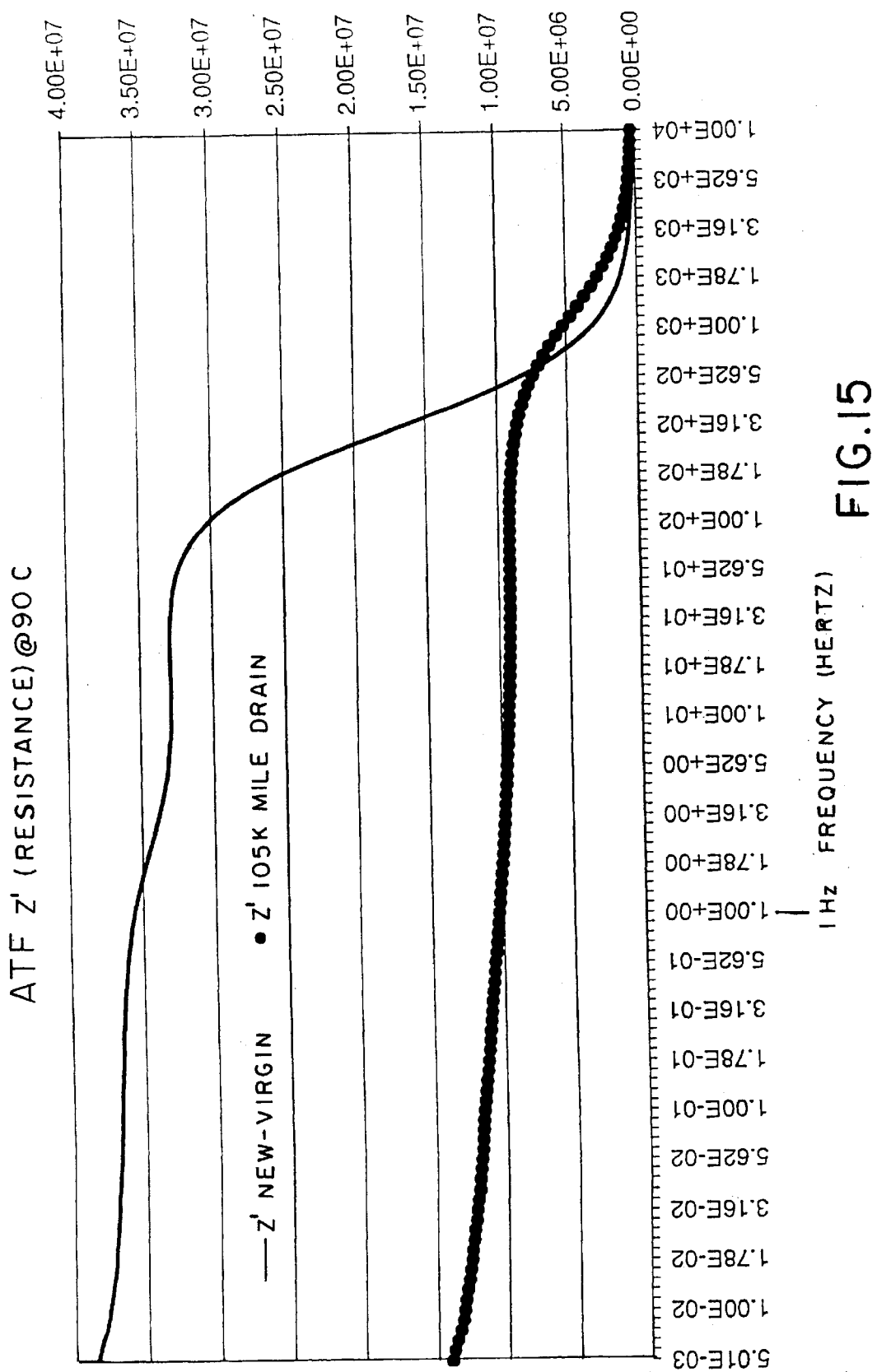

Referring to FIGS. 12 through 15, Bode plots are presented for measurements of resistance in Ohms as a function of the frequency of the applied AC voltage to the probe 12 for various vehicle lubricating fluids where the frequency of the applied voltage is swept over a frequency ranging from 14 millihertz to 10 kilohertz and families of curves are presented for uncontaminated fluid and fluid contaminated with engine coolant. FIG. 12 is presented for measurements of HDTT fluid at 90° Centigrade for new fluid; and, FIG. 13 is a plot of measurements for used HDTT fluid. FIG. 14 is a Bode plot for passenger car motor oil (PCMO) drained from a vehicle crank case after 3,400 miles of urban driving; and, FIG. 15 is a similar Bode plot for commercially available automatic transmission fluid new and used for 105,000 miles. It will be noted from FIGS. 12 through 15 that the curves for the base line or uncontaminated fluid are substantially flat in the range of frequencies from one hertz to 200 hertz; and, this characteristic of flatness does not change with the introduction of contamination. Therefore it has been determined that resistance measurements taken at frequencies in this range are indications of the bulk impedance of the fluid irrespective of the fluid condition.

However, it will be noted from FIGS. 12 through 15 that measurements of resistance taken at frequencies of about 30 millihertz and below encounter a steep rise in the curve with variations in frequency. Furthermore, it is noted from FIGS. 12 through 14 that the addition of contaminant to the measured fluid, although causing a shift downward in the curve does not result in the steep rise in the curve at the low frequencies. It is also observed that the curves remain generally flat or negative-going at the lower frequencies depending upon the level of contamination. Accordingly, it has been established that measurements of the resistance of the fluid at the lower frequencies, such as 30 millihertz, may be compared with the base line measurements for the fluid at the lower frequencies for making a valid determination whether the fluid is under the influence of contamination. This may be accomplished by subtracting the values obtained for the measured fluid in real time at the lower frequencies from the values obtained for the base line fluid and making a determination whether there is a significant difference and thus determining whether the fluid is contaminated.

In the present practice of the invention, the evaluation of the data presented in FIGS. 12 through 15 has indicated that if a minimum threshold difference is established, then an electrical comparison may be performed in real time and a continuous indication of the fluid condition provided electrically.

In the present practice of the invention the circuitry employed for the embodiment 10 of FIG. 1 employing the probe 12 and circuitry of FIGS. 3 and 4 provides a system which measures the current in the probe which varies proportionally to the changes in impedance; and, therefore the measurement of current is considered to be a valid analog of the change in resistance. In the present practice of the invention, a threshold value for the change in current $\Delta I = I_B - I_S$, where $I_S$ is the current measurement at the higher frequencies or frequencies above one hertz, has been established at a level of 4 nano amps. In other words, if a difference in current of at least four nano amps is detected by the system, the fluid is considered to be acceptable or in a non-contaminated condition and is suitable for continued usage. If, the system detects a $\Delta I$ or difference in current measured at frequently high frequencies and low frequencies of less than four nano amps, the system makes the determination that a significant level of contamination exists in the fluid and further usage should be prohibited and the system gives an indication that a fault condition exists.

Figure 2:
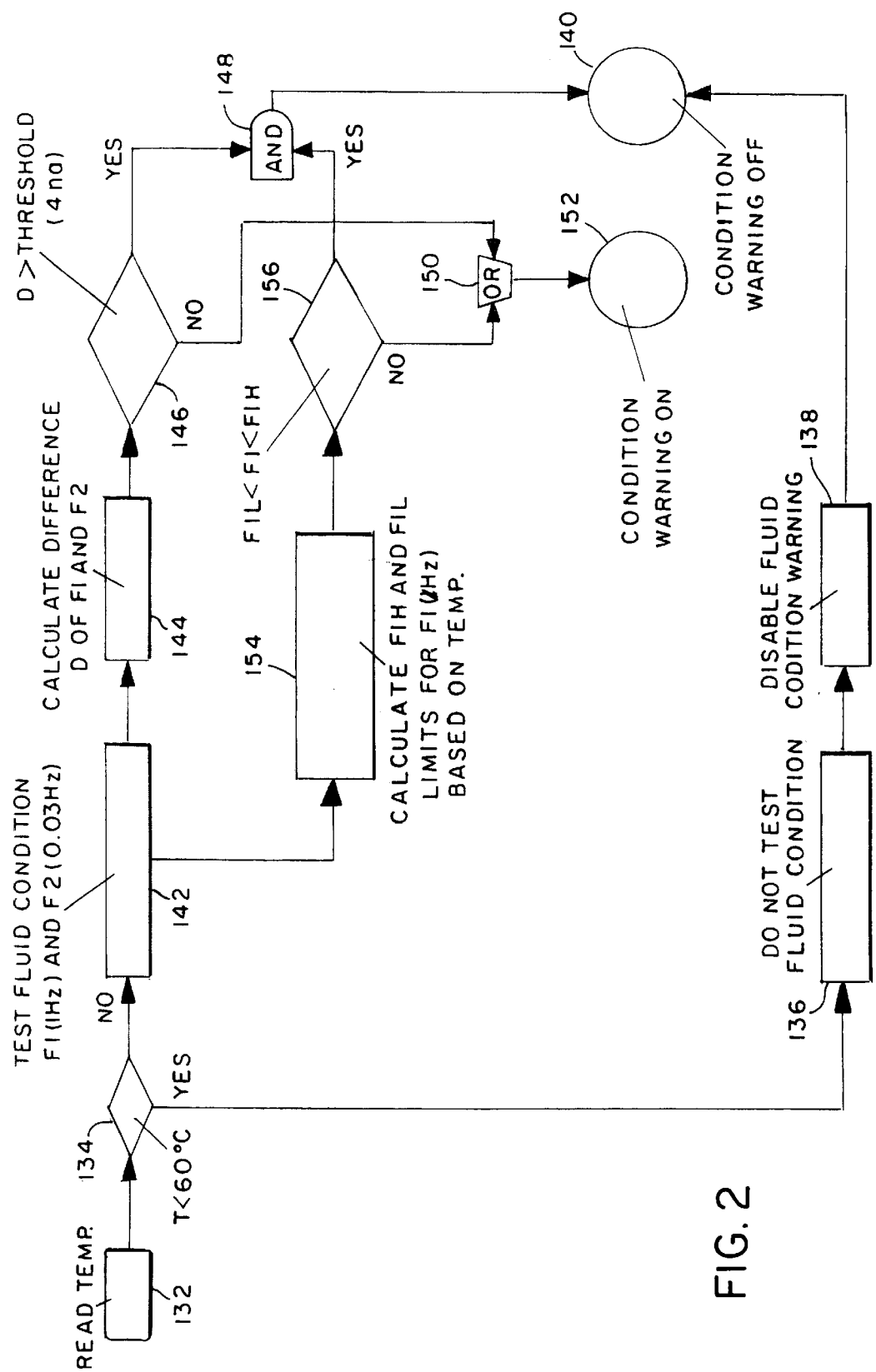
FIG. 2 is a block diagram of the computational algorithm for the system of FIG. 1.

Referring to FIG. 2, the system reads the temperature provided by temperature sensor 18 at step 132 and makes a determination at step 134 whether the temperature is below 60° Centigrade and if the result of the determination is positive, the system proceeds to step 136 and provides a fault indication and proceeds to step 138 to provide a warning disable signal which shuts down the condition warning light at 140.

If, a determination at step 134 is negative, the system proceeds to step 142 and tests the fluid by applying a voltage F1 at a first frequency of about one hertz to about 100 hertz to determine the bulk impedance of the fluid; and, a second signal F2 is applied at a frequency of 30 millihertz to determine the surface characteristics of the electrode of the probe. The system proceeds to step 144 to calculate the difference D of signals F1 and F2. The system them proceeds to step 146 to make a determination whether the difference D is greater than the threshold of four nano amps. If the determination of step 146 is positive the system provides an input signal to one input of AND gate 148. If the determination at step 146 is negative the system proceeds to an input an OR device 150 and illuminates a condition warning light at step 152.

At step 142 the signals F1 and F2 are also applied to the computer at step 154 and the upper and lower limits F1H and F1L are calculated for the higher frequency measurement F1 in accordance with the algorithms developed for the curves of FIG. 5. The measurement F1 for the higher frequency is then compared at step 156 with the values calculated in step 154; and, if the determination is made that the signal F1 is within the upper and lower limits established at step 154, the system proceeds to provide a signal to the second input of AND gate 148 and the condition warning light is disabled at step 140.

However, if the determination at step 156 is negative, the system proceeds to provide a signal through OR gate 150 to activate the warning light at 152.

Figure 10:
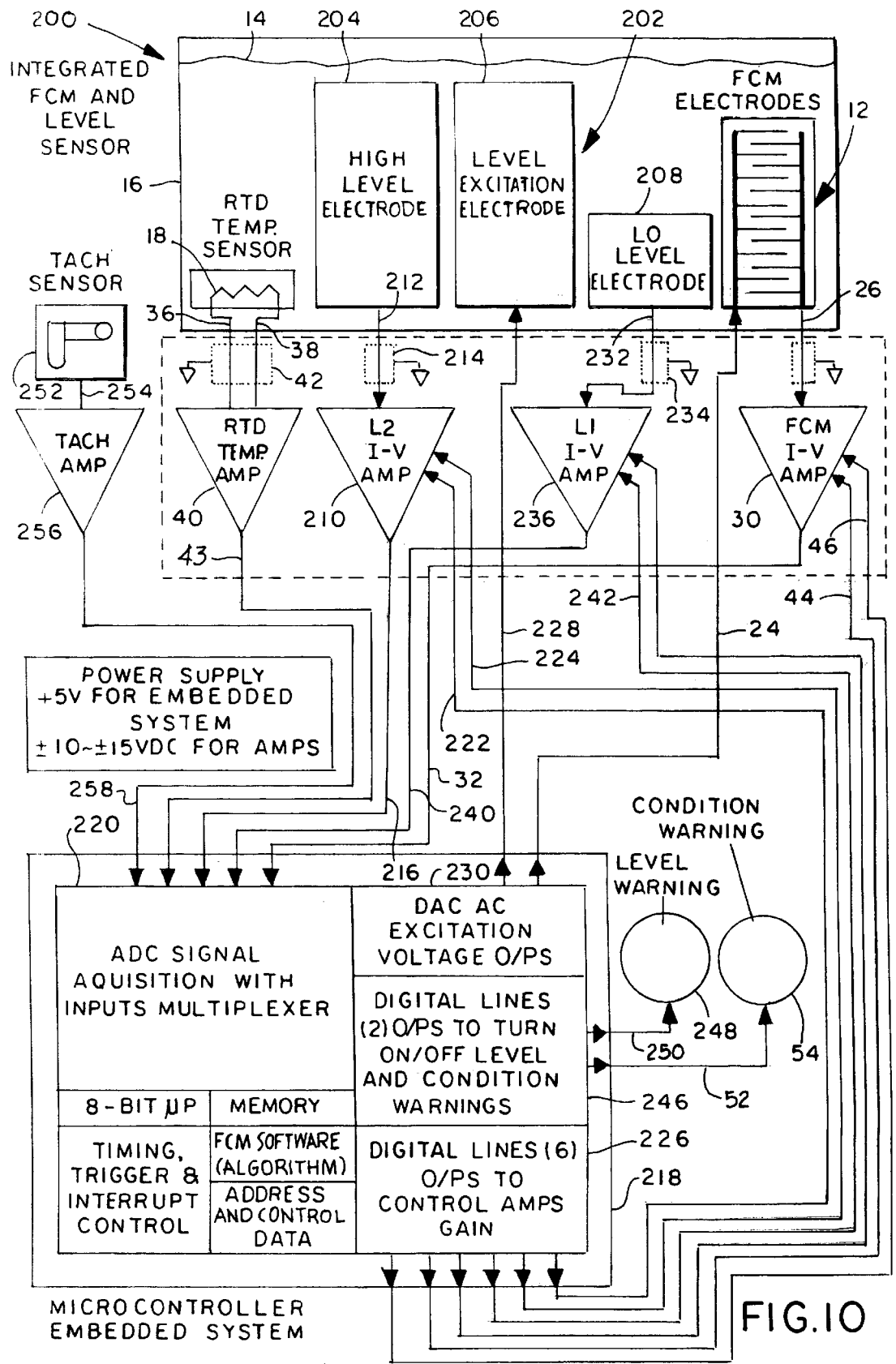
FIG. 10 is a block diagram of an alternate embodiment of the system of FIG. 1.

Referring to FIG. 10, another embodiment of the system is indicated generally at 200 which employs the probe 12 of the embodiment 10 of FIG. 1 and also the temperature sensor 18 of the embodiment of FIG. 1 disposed in the fluid 14 of receptacle 16 the embodiment of FIG. 10 includes a level sensor indicated generally at 202 which may be mounted commonly on the base structure 110 as shown in FIGS. 6 through 8.

Referring to FIG. 10, the level sensor 202 includes a high level electrode plate 204 and an excitation electrode plate 206 which are of the same size and configuration and disposed in spaced parallel arrangement as illustrated in FIG. 6. A low level electrode plate 208 is disposed preferably on the support structure 118 for the fluid condition probe 12 and is intended for providing electrical indication of an unacceptable low level of the fluid 14 in receptacle 16. In the present practice of the invention, the electrodes 204, 206, 208 are excited with the same one hertz voltage as employed for the bulk impedance excitation of the fluid condition monitor probe 12.

The electrode 204 provides an input to amplifier 210 along line 212 which is protected by grounded shield 214; and, the output of amplifier 210 is applied to the microcontroller indicated generally at 218 along line 26 to the signal acquisition section 220. Amplifier 210 receives gain control signals to provide auto ranging similar to amplifier 30 which signals are provided along lines 222, 224 from the digital control section 226 of the microcontroller 218.

The excitation electrode 206 receives a signal along line 228 from the AC excitation section 230 of the microcontroller 218. The low level electrode 208 provides an output signal along line 232 to grounded shield 234 to amplifier 236. The output of amplifier 236 is applied along line 240 to the input of signal acquisition section 220 of microcontroller 218; and, amplifier 236 receives gain control signals along lines 242, 244 from the amp gain control section 226 of the microcontroller 218. The gain control function for amplifier 236 may be similar to that described for amplifier 30 with reference to FIG. 3 to prove an "auto control" function.

The microcontroller 218 provides outputs from the digital section 246 to level warning light 248 along line 250 and to the condition warning light 54 along line 52.

If desired an optional tachometer sensor 252 may be employed which provides a signal along line 254 to a tachometer amplifier 256 whose output is applied to the signal acquisition section 220 along line 258.

Figure 11:
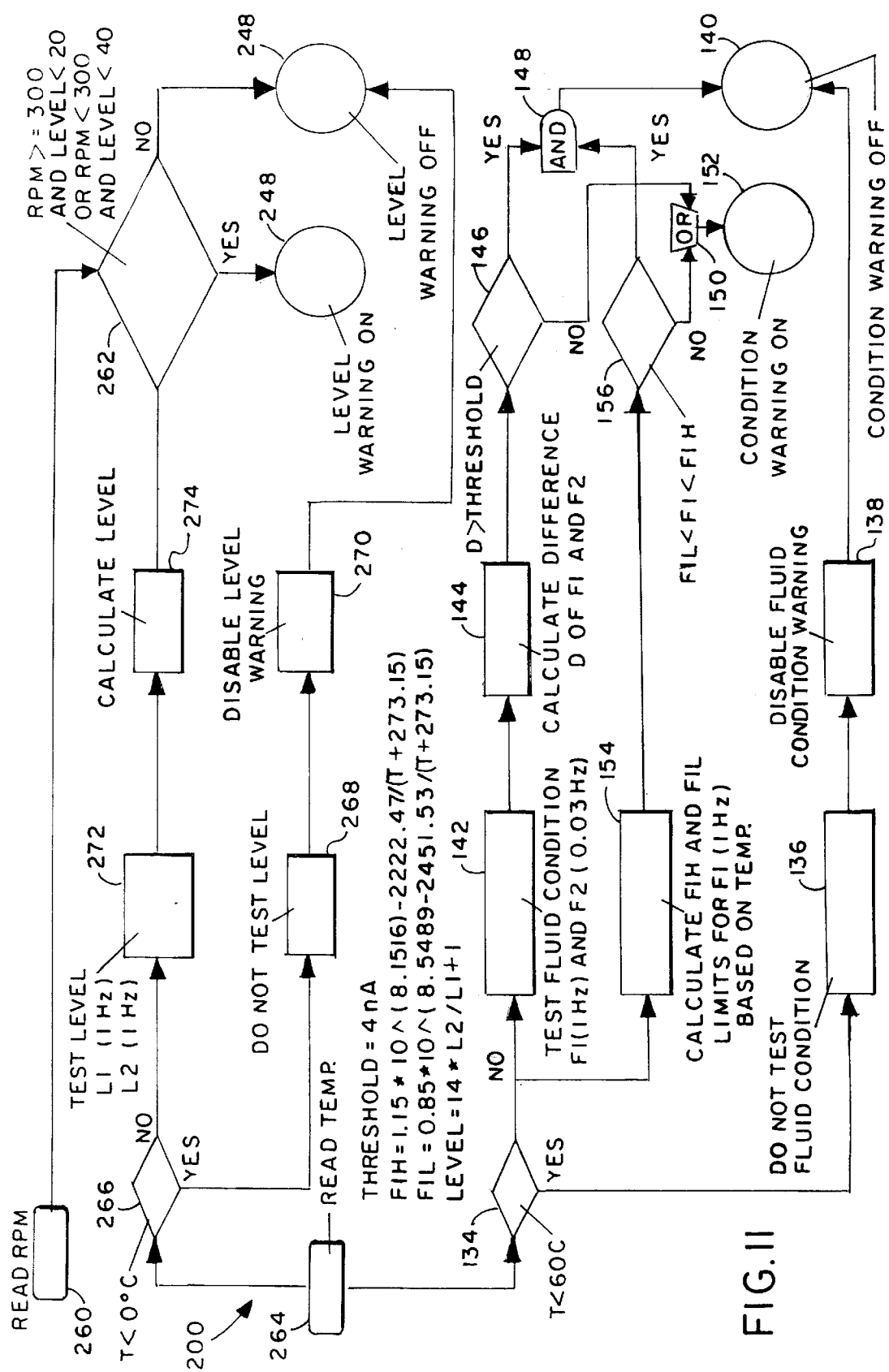
FIG. 11 is a block diagram of the algorithm employed in the system of FIG. 10.

Referring to FIG. 11, the operation of the system 200 of FIG. 10 is described in block flow diagram form where the system reads the RPM from the tachometer sensor 252 at step 260 and proceeds to step 262.

The system also reads the temperature from sensor 18 at step 264 and proceeds to step 266 where a determination is made whether the temperature is less than 0° Centigrade in which case the system proceeds to step 268 to provide a fault signal and proceeds to step 270 to disable the level warning light 248.

If the system determines at step 266 that the temperature of the fluid is at 0° Centigrade or higher the system proceeds to step 272 to test the level by reading the outputs from electrodes 204, 202 and the system calculates the fluid level at step 274. The system then proceeds to step 262 and tests to determine whether the RPM is equal to or greater than a threshold level set at 300 RPM and if the fluid level is less than a predetermined threshold set at 20. If the determination is affirmative, the system proceeds to activate the level warning light 248. If however, the determination is negative the system proceeds to turn off the level warning light 248.

The system also makes a determination at step 262 whether the RPM is less than the 300 level threshold and fluid level is less than the threshold level of 40. If this later determination is positive the system will energize the level warning light 248; however, if the determination is negative the system proceeds to turn off the level warning light 248.

The system thus operates at step 262 to provide energization of the level warning light if either of the tests performed is positive and disables the warning light if either of the tests is negative.

The temperature read by the system at step 264 is also input to step 134 as described with reference to FIG. 2 and the remaining function of the system 200 is identical to that of FIG. 2 as indicated by common reference numerals for corresponding steps.

The present invention thus provides a low cost and effective system for real time monitoring of the condition of a fluid in a fluid system, for example, lubricants in an engine or power transmission and provides continuing electrical indication of whether the fluid is suitable for a continued operation and optionally whether the fluid level is below an allowable minimum. The system employs electro-impedance spectroscopy whereby the fluid condition sensing probe has an array of parallel electrodes which are supplied with a constant level voltage at a first high frequency signal for determining the bulk impedance of the fluid and a second low frequency signal for determining the conditions on the electrode surface. The system electrically determines the difference in the current developed by the applied voltages and compares the current at the higher frequency with predetermined known conditions for the fluid and the current difference with a predetermined threshold to determine whether the fluid condition is acceptable for continued operation.

Although the invention has hereinabove been described with respect to the illustrated embodiments, it will be understood that the invention is capable of modification and variation and is limited only by the following claims.

What is claimed is:

1. A method of monitoring the condition of a fluid in a fluid system comprising:
    (a) forming a pair of electrodes and disposing said electrodes in spaced generally parallel arrangement;
    (b) immersing said electrodes at least partially in said fluid;
    (c) applying an oscillating substantially constant peak supply voltage sequentially at a first frequency of at least one Hertz and at a second frequency of less than one Hertz across said electrodes;
    (d) measuring the current flow at said first frequency representative of the bulk impedance of the fluid and said second frequency representative of the surface impedance of the electrodes and calculating the difference of said measured currents; and,
    (e) comparing said difference in measured currents with a reference level for a predetermined acceptable fluid condition and determining whether said comparison indicates a non-acceptable fluid condition and providing an electrical indication of the determination.

2. The method defined in claim 1, where in said step of disposing includes spacing said electrodes about 0.12 to about 1 mm apart.

3. The method defined in claim 1, wherein said step of applying an oscillating supply voltage at said first frequency includes applying said voltage in the range of about 10 hertz to about 10 kilohertz and at said second frequency in the range of about 1 millihertz to about 30 millihertz.

4. The method defined in claim 1, wherein said step of comparing and determining includes establishing that said voltage measured at first frequency is within predetermined limits established for the particular fluid and determining whether said difference in measured currents is greater than about 4 nano amperes.

5. The method defined in claim 1, further comprising the step of sensing the temperature of said fluid and disabling said step of applying when said sensed temperature is outside a predetermined range.

6. The method defined in claim 1 further comprising the step of detecting the level of said fluid and disabling said step of applying when said detected level is below a predetermined limit.

7. The method defined in claim 1, wherein said step of forming a pair of electrodes includes forming a pair of electrodes having a capacitance in the range of about 2 to about 20 pico farads ($2$–$20 \times 10^{-12}$ farads).

8. The method defined in claim 1, wherein said step of disposing said electrodes includes spacing said electrodes a predetermined distance apart.

9. The method defined in claim 1, wherein said step of disposing said electrodes includes spacing said electrodes apart a distance of about 0.12 mm to about 1 mm.

10. A method of monitoring the condition of a fluid in a fluid system comprising:
    (a) forming a pair of electrodes and disposing said electrodes in spaced generally parallel arrangement;
    (b) immersing said electrodes at least partially in said fluid;
    (c) flowing an oscillating current of a substantially constant peak magnitude sequentially at a first frequency of at least one Hertz and a second frequency of oscillation less than one Hertz through said electrodes for a certain period of time;
    (d) measuring the magnitude of voltage developed across said electrodes by said current at said first frequency representative of the bulk impedance of the fluid and at a second frequency representative of the impedance of the electrode surface and determining the difference of said measured voltages;
    (e) comparing said difference in measured voltages with a reference level for a predetermined acceptable fluid condition and determining whether said comparison indicates a non-acceptable fluid condition and indicating the results of said determining.

11. The method defined in claim 10 wherein said step of applying an oscillating voltage includes applying an oscillating sinusoidal voltage of a certain constant peak magnitude at said first and second oscillating frequencies for said lengths of time across said electrodes.

12. The method defined in claim 10, wherein the frequency of the said voltage applied to said electrodes is altered with the temperature of the said fluid in order to correct for alterations in the properties and condition of the fluid caused by changes in temperature.

13. The method defining claim 10, wherein the reference level is altered in a predetermined manner in accordance with the measured temperature of the fluid in order to correct for changes in the properties and conditions of the fluid caused by changes in temperature.

14. A method for sensing the condition of a fluid system comprising:
    (a) forming a pair of electrodes and disposing said electrodes in spaced arrangement;
    (b) immersing said electrodes at least partially in said fluid;
    (c) applying an oscillating voltage of a certain constant peak magnitude and certain oscillating frequency across said electrodes;
    (d) applying said voltage at a first frequency of oscillation of at least one Hertz for a certain period of time and measuring the magnitude of the current representative of the bulk impedance of the fluid;
    (e) applying said voltage at a second frequency of oscillation less than one Hertz for a certain period of time and measuring the magnitude of the current representative of the impedance of the electrode surface;
    (f) calculating the difference in magnitudes of said measured currents; and,
    (g) comparing the said difference in magnitudes of the measured currents to a reference level characteristic of a predetermined fluid condition and providing an electrical indication of the comparison and determining whether the comparison indicates a change in the condition of the fluid.

15. The method defined in claim 14, wherein said step of applying said voltage at a first frequency includes applying said voltage at a first frequency in the range of about 10 Hertz to about 10 kilohertz.

16. The method defined in claim 14, wherein said step of applying said voltage at a second frequency includes applying said voltage at a frequency in the range of about 1 millihertz to about 30 millihertz.

17. A method for sensing the condition of a fluid in a fluid system comprising:
    (a) forming a pair of electrodes and disposing said electrodes in spaced apart substantially parallel arrangement;
    (b) immersing said electrodes at least partially in said fluid;
    (c) applying an oscillating voltage of a certain constant peak magnitude and oscillating frequency;
    (d) applying said voltage at a first frequency of oscillation of at least ten (10) Hertz for measuring the bulk impedance of said fluid for a certain length of time and measuring the magnitude of the current developed at said first frequency for such certain length of time;
    (e) applying said voltage at a second frequency of oscillation less than said first frequency for measuring the surface impedance of the electrode and measuring the magnitude of the current at said second frequency for said certain length of time;
    (f) calculating the difference between said measured magnitudes of current at said first and second frequencies;
    (g) comparing the said difference in magnitudes of current to a reference level characteristic of a predetermined fluid condition to provide an electrical indication of the comparison and determining whether said comparison indicates a change in the condition of the fluid.

18. The method defined in claim 17, wherein said step of applying said voltage at a second frequency includes applying said voltage at a frequency of less than one (1) Hertz.

19. A method for sensing the condition of a fluid in a fluid system comprising:
    (a) forming a pair of electrodes and disposing said electrodes in spaced apart substantially parallel arrangement;
    (b) immersing said electrodes at least partially in said fluid;
    (c) applying an oscillating voltage of a certain constant peak magnitude and certain frequency across said electrodes;

(d) applying said voltage at a first relatively high frequency of oscillation for a certain length of time for measuring the bulk impedance of said fluid;

(e) measuring the magnitude of current at said first frequency and comparing said measured current with measured currents at said first frequency of acceptable fluid and determining if said current measured at said first frequency is within acceptable limits;

(f) applying said voltage at a second relatively low frequency of oscillation for measuring the electrode surface impedance;

(g) measuring the magnitude of current at said second frequency of oscillation and calculating the difference in said current measured at said first and second frequencies;

(h) comparing said calculated difference in currents to a reference level characteristic of a predetermined fluid condition and providing an electrical indication of the comparison and determining whether said comparison indicates a significant change in the condition of the fluid.

* * * * *